(12) United States Patent
Wei

(10) Patent No.: US 8,712,534 B2
(45) Date of Patent: Apr. 29, 2014

(54) COMBINED HIGH AND LOW FREQUENCY STIMULATION THERAPY

(71) Applicant: Medtronic, Inc., Minneapolis, MN (US)

(72) Inventor: Xuan K. Wei, Minnetonka, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 13/658,240

(22) Filed: Oct. 23, 2012

(65) Prior Publication Data

US 2013/0110194 A1    May 2, 2013

Related U.S. Application Data

(60) Provisional application No. 61/553,082, filed on Oct. 28, 2011.

(51) Int. Cl.
*A61N 1/00* (2006.01)
(52) U.S. Cl.
USPC .......................................................... 607/46

(58) Field of Classification Search
USPC .............................................. 607/46, 41, 3, 62
See application file for complete search history.

(56) References Cited

U.S. PATENT DOCUMENTS

| | | | |
|---|---|---|---|
| 6,928,320 B2 | 8/2005 | King | |
| 2005/0143789 A1 | 6/2005 | Whitehurst et al. | |
| 2007/0067004 A1* | 3/2007 | Boveja et al. | 607/45 |
| 2009/0054950 A1 | 2/2009 | Stephens | |
| 2009/0222053 A1* | 9/2009 | Gaunt et al. | 607/3 |
| 2011/0282412 A1* | 11/2011 | Glukhovsky et al. | 607/41 |

* cited by examiner

*Primary Examiner* — Robert N Wieland
(74) *Attorney, Agent, or Firm* — Shumaker & Sieffert, P.A.

(57) ABSTRACT

In some examples, the disclosure relates to system, devices, and techniques for delivering electrical stimulation therapy to treat patient disorders characterized by overactive nerve activity. In one example, the stimulation therapy may include high frequency and low frequency stimulation. The high frequency stimulation may be configured to substantially block overactive pathological nerve activity of the patient and the combination of the high frequency and low frequency simulation may be configured to result in nerve activity that mimics non-pathological nerve activity.

22 Claims, 8 Drawing Sheets

COMBINED HIGH AND LOW FREQUENCY STIMULATION THERAPY

CROSS-REFERENCE TO RELATED APPLICATIONS

The present application claims priority to U.S. Provisional Patent Application No. 61/553,082, filed Oct. 28, 2011, which application is hereby incorporated by reference as if re-written in its entirety.

TECHNICAL FIELD

The disclosure relates to medical devices and, more particularly, to programmable medical devices that deliver electrical stimulation therapy to a patient.

BACKGROUND

A variety of therapies, such as neurostimulation or therapeutic agents, e.g., drugs, may be delivered to a patient to treat chronic or episodic pain. Neurostimulation is typically delivered by an implantable medical device (IMD). An IMD delivers neurostimulation therapy via electrodes, which are coupled to the IMD by one or more leads, or carried by the IMD housing in the case of a leadless stimulator. The number and positions of the leads and electrodes is largely dependent on the type or cause of the pain, and the type of neurostimulation delivered to treat the pain. In general, an IMD may deliver neurostimulation therapy in the form of electrical stimulation signals such as pulses and continuous waveforms.

SUMMARY

In general, the disclosure is directed to systems, devices and techniques for delivering electrical stimulation therapy to a patient. In some examples, the therapy may include first electrical stimulation defined by a relatively high frequency that is combined with the delivery of second electrical stimulation defined by a relatively low frequency. The frequency of the first electrical stimulation may be selected to substantially block overactive pathological nerve activity, and the frequency of the first and second therapies may be selected such that the combination of the first and second therapies modulates the nerve activity to mimic non-pathological activity. In this manner, the stimulation therapy delivered by the medical device to a patient may be used, in some cases, to treat or manage patient disorders that may be characterized by overactive nerve activity.

In one example, the disclosure relates to a method comprising delivering a first stimulation therapy to a patient via a medical device, wherein the high frequency stimulation therapy is defined by a first frequency; and delivering a second stimulation therapy the patient via the medical device in combination with the delivery of the first stimulation therapy, wherein the second stimulation therapy is defined by a second frequency that is less than the first frequency, and wherein the first frequency and second frequency are configured such that the first stimulation therapy substantially blocks overactive pathological nerve activity of the patient and the combination of the first and second therapies results in nerve activity that mimics non-pathological nerve activity.

In another example, the disclosure relates to a system comprising a therapy module configured to deliver a first stimulation therapy to a patient and a second stimulation therapy, wherein the first stimulation therapy is defined by a first frequency and the second stimulation therapy is defined by a second frequency that is less than the first frequency; and a processor configured to control the therapy module to deliver the first and second stimulation therapies in combination with one another, wherein the first frequency and second frequency are configured such that the first stimulation therapy substantially blocks overactive pathological nerve activity of the patient and the combination of the first and second therapies results in nerve activity that mimics non-pathological nerve activity.

In another example, the disclosure relates to a system comprising means for delivering a first stimulation therapy to a patient via a medical device, wherein the high frequency stimulation therapy is defined by a first frequency; and means for delivering a second stimulation therapy the patient via the medical device in combination with the delivery of the first stimulation therapy, wherein the second stimulation therapy is defined by a second frequency that is less than the first frequency, and wherein the first frequency and second frequency are configured such that the first stimulation therapy substantially blocks overactive pathological nerve activity of the patient and the combination of the first and second therapies results in nerve activity that mimics non-pathological nerve activity.

In another example, the disclosure relates to a non-transitory computer-readable storage medium comprising instructions that cause a processor to control a therapy module to deliver a first stimulation therapy to a patient via a medical device, wherein the high frequency stimulation therapy is defined by a first frequency; and control the therapy module to deliver a second stimulation therapy the patient via the medical device in combination with the delivery of the first stimulation therapy, wherein the second stimulation therapy is defined by a second frequency that is less than the first frequency, and wherein the first frequency and second frequency are configured such that the first stimulation therapy substantially blocks overactive pathological nerve activity of the patient and the combination of the first and second therapies results in nerve activity that mimics non-pathological nerve activity.

The details of one or more examples of the invention are set forth in the accompanying drawings and the description below. Other features, objects, and advantages of the invention will be apparent from the description and drawings, and from the claims.

DETAILED DESCRIPTION

Figure 1:
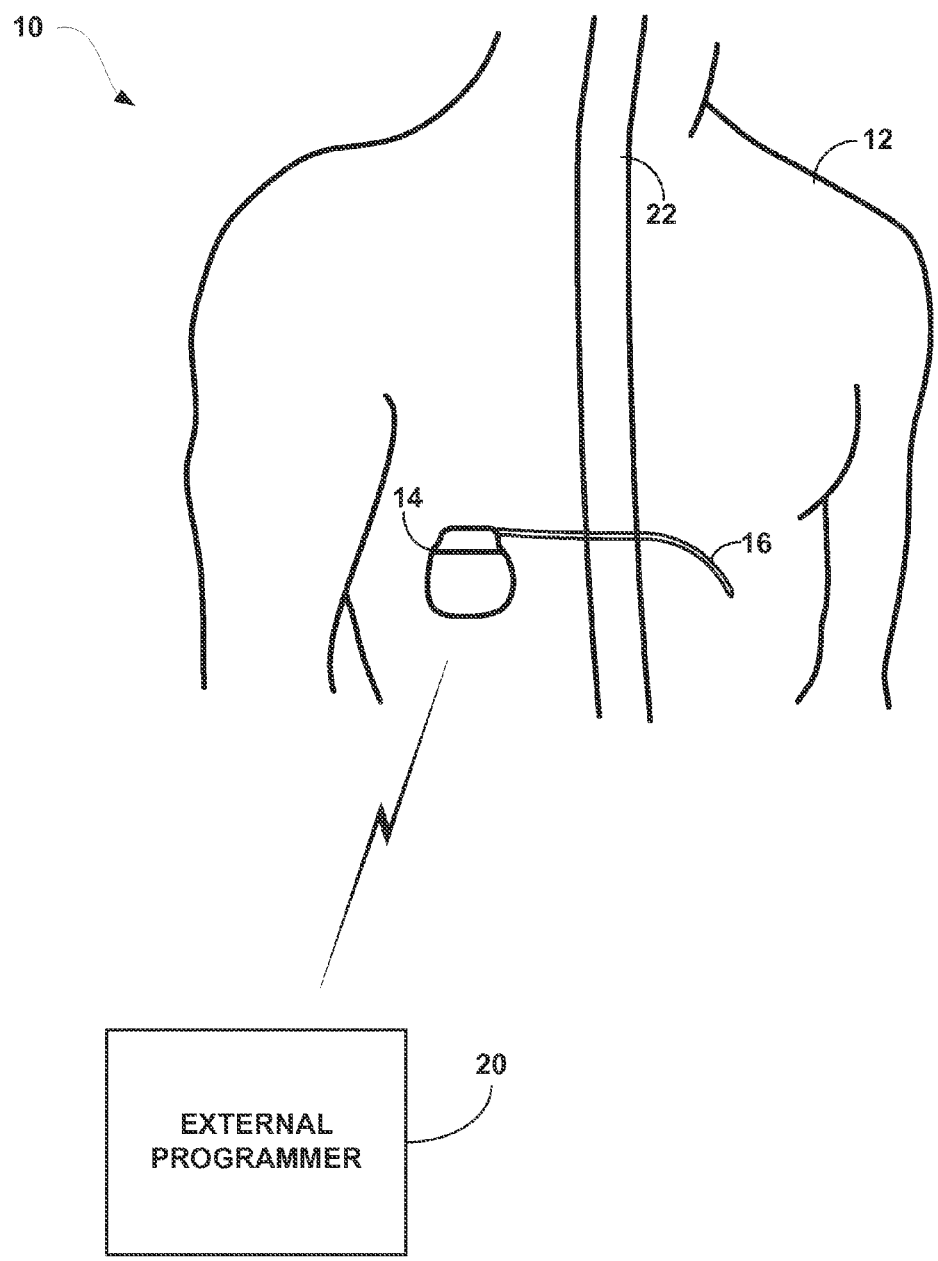
FIG. 1 is a conceptual diagram illustrating an example implantable stimulation system.

In general, the disclosure is directed to systems, devices and techniques for delivering electrical stimulation therapy to a patient. In some examples, the therapy may include first electrical stimulation defined by a relatively high frequency that is combined with the delivery of second electrical stimulation defined by a relatively low frequency. The frequency of the first electrical stimulation may be selected to substantially block overactive pathological nerve activity, and the frequency of the first and second therapies may be selected such that the combination of the first and second therapies modulates the nerve activity to mimic non-pathological activity. In this manner, the stimulation therapy delivered by the medical device to a patient may be used, in some cases, to treat or manage patient disorders that may be characterized by overactive nerve activity.

A medical device, such as an IMD, may deliver electrical stimulation therapy to a patient for a variety of reasons. In some examples, to treat a patient disorder, values for one or more stimulation parameters associated with the electrical stimulation therapy may be defined such that the stimulation activates nerve activity to increase nerve activity of, e.g., a peripheral nerve of the patient. Put another way, the stimulation may activate nerve fibers rather than inhibits spontaneous nerve activity. In such cases, the increased nerve activity resulting from the delivery of electrical stimulation may effectively treat patient pain or other condition.

However, in some examples, nerve activity considered overactive or elevated activity may be associated with be associated with one or more symptoms of a patient disorder. For example, symptoms of some sensory disorders may result from, or be associated with, overactive afferent nerve activity of a patient, e.g., in the sense that symptoms of the sensory disorder may frequently occur or manifest themselves when the afferent nerve activity of the patient is elevated. In this respect, such overactive afferent nerve activity may be referred to as pathological overactive afferent nerve activity or, more generally, pathological overactive nerve activity. The pathological nerve activity may be elevated continuously or only on an intermittent basis, and the nerve activity may be associated with a single nerve or group of nerves that form a pathway for propagation of signals. Symptoms and disorders that may be associated with pathological afferent nerve activity may include pain, such as, leg or back pain, interstitial cystitis, overactive bladder, chronic pelvic pain, abacterial chronic prostatitis (Type IIIB), and neuralgias.

Similarly, in some cases, symptoms of some motor disorders may result from, or be associated with, overactive efferent nerve activity of a patient. In this respect, such overactive efferent nerve activity may be referred to as pathological overactive efferent nerve activity or, more generally, pathological overactive nerve activity. The pathological nerve activity may be elevated continuously or only on an intermittent basis, and the nerve activity may be associated with a single nerve or group of nerves that form a pathway for propagation of signals. Symptoms and disorders that may be associated with pathological efferent nerve activity may include spasticity, tics, choreas, and intractable hiccups.

In each case, whether it is a sensory disorder or motor disorder, the pathological nerve activity of a patient may be considered overactive. Accordingly, treating a disorder associated with overactive nerve activity by only delivering electrical stimulation to active nerve fibers rather than inhibit spontaneous nerve activity may not effectively manage or treat the disorder as such stimulation therapy adds information or activity to the nerve activity without subtracting the pathological nerve activity. Furthermore, while parameters of stimulation therapy may be selected such that the therapy delivered to the patient substantially blocks all nerve activity, such stimulation only results in stopping substantially all nerve activity rather than changing the pathological nerve activity to non-pathological nerve activity.

In accordance with some examples of the disclosure, example techniques are describe for stimulation therapy to a patient via a medical device to substantially block pathological nerve activity while at the same time causing nerve activity that mimics non-pathological nerve activity. For example, a medical device may deliver high frequency stimulation in combination with low frequency stimulation to one or more nerve sites of a patient. As used herein, the use of the terms "high" and "low" with regard to the described frequencies express the relative condition of the frequency of the high frequency stimulation being greater than the frequency of the low frequency stimulation.

As will be described below, in some examples, the frequency of the high frequency stimulation may be selected such that the delivery of the high frequency stimulation to a nerve site substantially blocks nerve activity. In some examples, the high frequency electrical stimulation may be defined by a frequency between about 1 kilohertz (kHz) and 50 kHz. Additionally, the frequency of the low frequency stimulation may be selected such that the combination of the high and low frequency stimulation results in nerve activity that mimics non-pathological nerve activity.

In some examples, a medical device may be deliver a high frequency electrical stimulation therapy to a first nerve site, e.g., via one or more first electrodes on a lead, and a low frequency electrical stimulation therapy to a second nerve site, e.g., via one or more second electrode on the same or different lead, along the same neural pathway. The frequency of the high frequency stimulation therapy may be selected to substantially block nerve activity at the first nerve site along the neural pathway. Such high frequency stimulation may block both efferent and afferent activity at the first nerve site. In this manner, the high frequency stimulation may prevent nerve activity from being propagated across the first nerve site when the high frequency stimulation is being delivered.

In combination with the high frequency stimulation, low frequency stimulation may be delivered distally and/or proximally of the first nerve site where the high frequency stimulation is delivered to block nerve activity. In the case of pathological afferent nerve activity, the low frequency stimulation may be delivered to a nerve site proximal the nerve site where pathological nerve activity is blocked via the high frequency stimulation. Conversely, in the case of pathological efferent nerve activity, the low frequency stimulation may be delivered to a nerve site distal the nerve site where pathological nerve activity is blocked via the high frequency stimulation. The frequency of the low frequency stimulation may be selected to activate nerve fibers to induce nerve activity that mimics non-pathological nerve activity.

In another example, a medical device may deliver electrical stimulation to a single nerve site of the patient, e.g., using the same electrode(s) on a lead. In such examples, the combination of the first and second therapies may refer to the delivery of a stimulation signal including a plurality of "envelopes" delivered according to the low frequency defined for the stimulation. Within each "envelope" is a plurality of individual stimulation pulses delivered according to the high frequency defined for the stimulation. In some examples, each "envelope" may also be referred to as a burst defined by a plurality stimulation pulses delivered during the burst. A series of bursts may be delivered according to a low frequency and the plurality of stimulation pulses within each burst are delivered according to a high frequency, where the high frequency is selected such that the plurality of stimulation pulses within a burst substantially blocks pathological nerve activity at the nerve site. The frequency that the envelopes or bursts are delivered may be selected such that the nerve activity not blocked by the envelopes or bursts (e.g., the nerve activity that occurs during the time that an envelope or burst is not being delivered to the site) over a period of time mimics non-pathological nerve activity.

Put another way, the delivery of high frequency electrical stimulation may be cycled on and off by the medical device over a period of time. During that period of time, the frequency and timing with which the high frequency stimulation in turned on to block pathological nerve activity may be such that the nerve activity not blocked by the high frequency stimulation (e.g., during the off period of the cycle) may mimic non-pathological nerve activity. In this manner, the stimulation therapy delivered to a patient to treat a disorder characterized by overactive nerve activity by selectively suppressing of the nerve activity on an intermittent basis such that the unsuppressed nerve activity mimics non-pathological nerve activity.

FIG. 1 is a schematic diagram illustrating an example implantable stimulation system 10 configured to delivery electrical stimulation to patient 12. Although the techniques described in this disclosure are generally applicable to a variety of medical devices including external and implantable medical devices (IMDs), application of such techniques to IMDs and, more particularly, implantable electrical stimulators such as neurostimulators will be described for purposes of illustration. More particularly, the disclosure will refer to an implantable neurostimulation system for purposes of illustration, but without limitation as to other types of medical devices.

As shown in FIG. 1, system 10 includes an IMD 14 and external programmer 20 shown in conjunction with a patient 12, who is ordinarily a human patient. In the example of FIG. 1, IMD 14 is an implantable electrical stimulator that delivers neurostimulation therapy to patient 12, e.g., for relief of chronic pain or other symptoms. In some examples, IMD 14 may deliver stimulation therapy to patient 12 to treat one or more sensory or motor disorders characterized at least in part by overactive nerve activity. Again, although FIG. 1 shows an IMD, other examples may include an external stimulator, e.g., with percutaneously implanted leads.

Electrical stimulation energy, which may be constant current or constant voltage based pulses, for example, is delivered from IMD 14 to one or more targeted locations within patient 12 via one or more electrodes (not shown) of implantable lead 16. The parameters for a program that controls delivery of stimulation energy by IMD 14 may include information identifying which electrodes have been selected for delivery of stimulation according to a stimulation program, the polarities of the selected electrodes, i.e., the electrode configuration for the program, and voltage or current amplitude, pulse rate, pulse shape, and pulse width of stimulation delivered by the electrodes. Delivery of stimulation pulses will be described for purposes of illustration. However, stimulation may be delivered in other forms, such as continuous waveforms.

In the example of FIG. 1, lead 16 may carry one or more electrodes that are placed adjacent to the target tissue. One or more electrodes may be disposed at a distal tip of lead 16 and/or at other positions at intermediate points along lead 16, for example. Electrodes of lead 16 transfer electrical stimulation generated by an electrical stimulation generator in IMD 14 to tissue of patient 12. The electrodes may be electrode pads on a paddle lead, circular (e.g., ring) electrodes surrounding the body of the lead, conformable electrodes, cuff electrodes, segmented electrodes, or any other type of electrodes capable of forming unipolar, bipolar or multipolar electrode configurations for therapy. In general, ring electrodes arranged at different axial positions at the distal ends of lead 16 will be described for purposes of illustration.

Lead 16 may be configured to deliver stimulation energy generated by IMD 14 to stimulate one or more peripheral nerves of patient 12, e.g., in the form of peripheral nerve stimulation (PNS). PNS may be used to treat patients suffering from intractable pain secondary to nerve damage isolated to a single nerve. PNS may including locating a group of electrodes in very close proximity to, e.g., in contact with, and approximately parallel to a major nerve in the subcutaneous tissue. PNS may also include placing a group of electrodes in very close proximity to a nerve that may be deeper in the limb, sometimes near to blood vessels. Placing electrodes in very close proximity to the nerve may ensure that only fibers within that nerve are activated at low amplitudes.

PNS electrodes may be located on percutaneous leads, but for stability and to prevent stimulation of other tissues proximate to the target peripheral nerve, PNS electrodes may be located within insulative material that wraps around a nerve, i.e., in so-called cuff electrodes, or on one surface of a flat paddle of insulative material placed under a nerve. In any case, the electrodes for PNS may be placed in close proximity to the nerve proximal from the source of damage or pain, e.g., closer to the spinal cord than the region of damage or pain. Upper extremity nerves that may be treated with PNS include the ulnar nerve, median nerve, radial nerve, tibial nerve, occipital nerve, and common peroneal nerve. When PNS is delivered to treat pain, one or more electrodes may be implanted proximate to or in contact with a specific peripheral nerve or branch that is responsible for the pain sensation.

As will be described below, IMD 14 may deliver electrical stimulation therapy to one or more nerve sites of patient 12 to treat or manage sensory and/or motor disorders. In some examples, IMD 14 may deliver therapy to treat one or more patient disorders characterized by pathological overactive afferent or efferent activity. Example sensory disorders that may be characterized by overactive afferent nerve activity may include chronic pelvic pain, interstitial cystitis, abacterial chronic prostatitis (Type IIIB), neuralgias, and other chronic pain conditions, are characterized by pathological afferent activity. In such cases, the abnormal overactive afferent activity may cause pain, overwhelms central processing and inhibit associated neural activities through reflex pathways. Example motor disorders that may be characterized by overactive afferent nerve activity may include spasticity, tics, choreas, intractable hiccups and the like.

As will be described in greater detail below, in some examples, to treat such disorders, IMD 14 may deliver high frequency stimulation (e.g., PNS) to patient 12 via lead 16 in combination with the delivery of low frequency stimulation to patient 12. IMD 14 may be configured to deliver the high frequency stimulation to the same or nerve site as the low frequency stimulation. The high frequency stimulation may be configured to substantially block pathological nerve activity. Furthermore, the combination of the low and high frequency stimulation therapy may be configured to result in nerve activity that mimics non-pathological nerve activity. While examples of the disclosure are primarily described with regard to PNS, examples are not limited as such. For example, IMD 14 may be configured to deliver electrical stimulation to one or more spinal cord nerve sites in addition to or as an alternative to peripheral nerve sites. In some examples, the stimulation may take of the form of deep brain stimulation (DBS), peripheral nerve field stimulation (PNFS), subcutaneous electrical stimulation (SQS), autonomic nerve stimulation, spinal cord stimulation, and/or organ stimulation.

Lead 16 within patient 12 directly or indirectly (e.g., via a lead extension) coupled to IMD 14. Alternatively, as mentioned above, lead 16 may be implanted and coupled to an external stimulator, e.g., through a percutaneous port. In some cases, an external stimulator is a trial or screening stimulation that is used on a temporary basis to evaluate potential efficacy to aid in consideration of chronic implantation for a patient. In additional examples, IMD 14 may be a leadless stimulator with one or more arrays of electrodes arranged on a housing of the stimulator rather than leads that extend from the housing.

IMD 14 delivers electrical stimulation therapy to patient 12 via selected combinations of electrodes carried by lead 16. The target tissue for the electrical stimulation therapy may be any tissue affected by electrical stimulation energy, which may be in the form of electrical stimulation pulses or waveforms. Again, while examples of the disclosure are primarily described with regard to PNS, target nerve sites may include nerve sites of the spinal cord 22, including dorsal column and dorsal root nerves. For example, in addition to or as an alternative to delivering stimulation to one or more peripheral nerves, nerve sites for electrical stimulation delivered via lead 18 may be part of spinal cord 22. In some examples, the target nerve sites for electrical stimulation delivered via lead 16 may dorsal root or other nerve roots that branch off spinal cord 22. Lead 16 may be introduced proximate spinal cord 22 via any suitable region, such as the thoracic, cervical or lumbar regions.

The deployment of electrodes via lead 16 is described for purposes of illustration, but arrays of electrodes may be deployed in different ways. For example, a housing associated with a leadless stimulator may carry arrays of electrodes, e.g., rows and/or columns (or other patterns). Such electrodes may be arranged as surface electrodes, ring electrodes, or protrusions. As a further alternative, electrode arrays may be formed by rows and/or columns of electrodes on one or more paddle leads. In some examples, electrode arrays may include electrode segments, which may be arranged at respective positions around a periphery of a lead, e.g., arranged in the form of one or more segmented rings around a circumference of a cylindrical lead.

The electrical stimulation delivered by IMD 14 may take the form of electrical stimulation pulses or continuous stimulation waveforms, and may be characterized by controlled voltage levels or controlled current levels, as well as pulse width and pulse rate (also referred to as pulse frequency). In the case of stimulation including envelopes or bursts including a plurality of pulses, the envelopes may be characterized by rate, and/or duration. In some examples, IMD 14 generates and delivers stimulation therapy according to one or more programs. A program defines values for one or more parameters that define an aspect of the therapy delivered by IMD 14 according to that program. For example, a program that controls delivery of stimulation by IMD 14 in the form of pulses may define a voltage or current pulse amplitude, a pulse width, a pulse rate, for stimulation pulses delivered by IMD 14 according to that program. Moreover, therapy may be delivered according to multiple programs, wherein multiple programs are contained within each of a plurality of groups.

Each program group may support an alternative therapy selectable by patient 12, and IMD 14 may deliver therapy according to the multiple programs. IMD 14 may rotate through the multiple programs of the group when delivering stimulation such that numerous conditions of patient 12 are treated. As an illustration, in some cases, stimulation pulses formulated according to parameters defined by different programs may be delivered on a time-interleaved basis. For example, a group may include a program directed to leg pain, a program directed to lower back pain, and a program directed to abdomen pain. Alternatively, multiple programs may contribute to an overall therapeutic effect with respect to a particular type or location of pain. In this manner, IMD 14 may treat different symptoms substantially simultaneously or contribute to relief of the same symptom.

A user, such as a clinician or patient 12, may interact with a user interface of external programmer 20 to program IMD 14. Programming of IMD 14 may refer generally to the generation and transfer of commands, programs, or other information to control the operation of IMD 14. For example, external programmer 20 may transmit programs, parameter adjustments, program selections, group selections, or other information to control the operation of IMD 14, e.g., by wireless telemetry. Again, a program may be characterized by an electrode combination, electrode polarities, voltage or current amplitude, pulse width, pulse rate, pulse shape, envelope frequency, and/or envelope duration. A group may be characterized by multiple programs that are delivered simultaneously or on an interleaved or rotating basis.

In some cases, external programmer 20 may be characterized as a physician or clinician programmer if it is primarily intended for use by a physician or clinician. In other cases, external programmer 20 may be characterized as a patient programmer if it is primarily intended for use by a patient. A patient programmer is generally accessible to patient 12 and, in many cases, may be a portable device that may accompany the patient throughout the patient's daily routine. In general, a physician or clinician programmer may support selection and generation of programs by a clinician for use by stimulator 14, whereas a patient programmer may support adjustment and selection of such programs by a patient during ordinary use.

IMD 14 may be constructed with a biocompatible housing, such as titanium or stainless steel, or a polymeric material such as silicone or polyurethane, and surgically implanted at a site in patient 12 near the pelvis. IMD 14 may also be implanted in patient 12 at a location minimally noticeable to patient 12. Alternatively, IMD 14 may be external with percutaneously implanted lead(s). For SCS or PNS, IMD 14 may be located in the lower abdomen, lower back, upper buttocks, or other location to secure IMD 14. Lead 16 may be tunneled from IMD 14 through tissue to reach a location adjacent to a target nerve site for stimulation delivery.

Implantable stimulation system 10 is not limited to that of one leads, but instead may include zero, two, three, four, five or more than five leads. For example, system 10 may include a second lead in addition to lead 16. In such a configuration, IMD 14 may deliver stimulation via combinations of electrodes carried by both leads, or a subset of the two leads. The electrode configuration may be multipolar (e.g., bipolar) or unipolar arrangements. The second lead may include a greater number of electrodes than lead 16 and be positioned on either side of lead 16. The number and configuration of all leads may be stored within external programmer 20 to allow programmer 20 to appropriately program stimulation therapy or assist in the programming of stimulation therapy.

Figure 2:
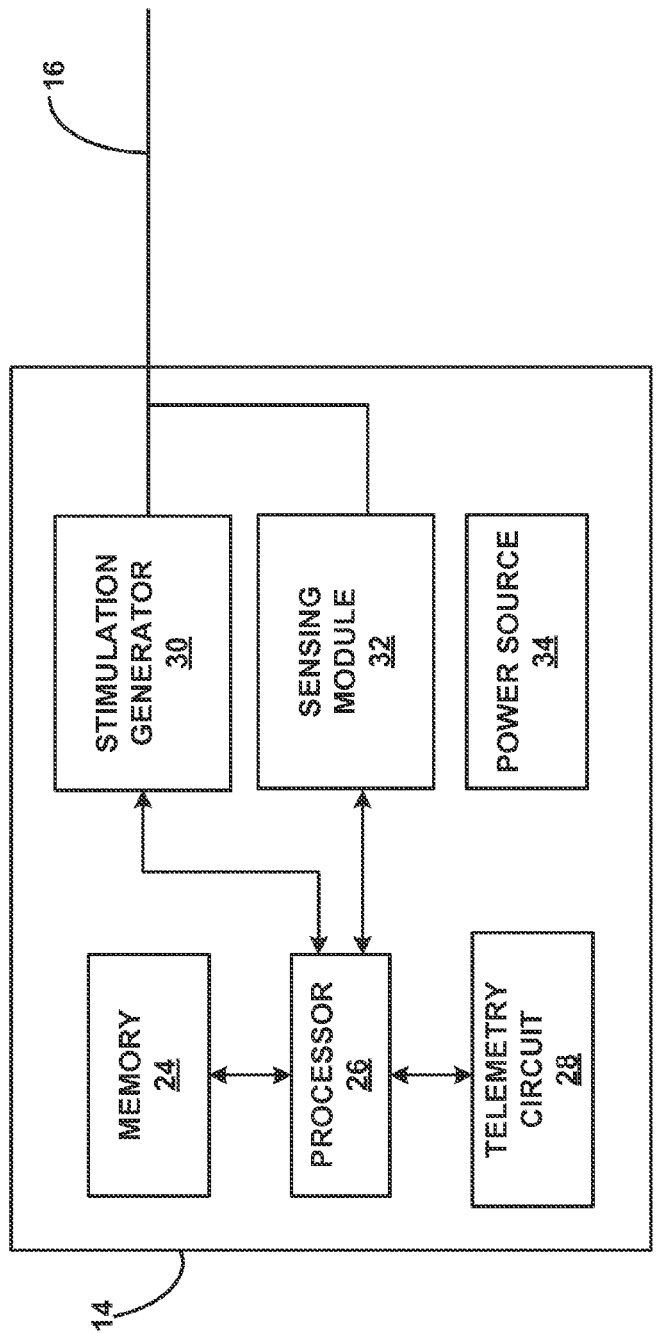
FIG. 2 is a functional block diagram illustrating various components of an example implantable electrical stimulator.

FIG. 2 is a functional block diagram illustrating various components of an IMD 14. In the example of FIG. 2, IMD 14 includes memory 24, processor 26, telemetry circuit 28, stimulation generator 30, sensing module 32, and power source 34. The stimulation generator 30 forms what may also be referred to as a therapy delivery module.

Memory 24 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital media. Memory 24 may store instructions for execution by processor 26, stimulation therapy data, information regarding evoked signals sensed at one or more locations on the dorsal columns, and any other information regarding therapy or patient 12. Therapy information may be recorded for long-term storage and retrieval by a user, and the therapy information may include any data created by or stored in IMD 14. Memory 24 may include separate memories for storing instructions, sensed signal information, program histories, and any other data that may benefit from separate physical memory modules.

Memory 24 may be considered, in some examples, a non-transitory computer-readable storage medium comprising instructions that cause one or more processors, such as, e.g., processor 26, to implement one or more of the example techniques described in this disclosure. The term "non-transitory" may indicate that the storage medium is not embodied in a carrier wave or a propagated signal. However, the term "non-transitory" should not be interpreted to mean that memory 24 is non-movable. As one example, memory 24 may be removed from IMD 14, and moved to another device. In certain examples, a non-transitory storage medium may store data that can, over time, change (e.g., in RAM).

Processor 26 controls stimulation generator 30 to deliver electrical stimulation via electrode combinations formed by electrodes. For example, stimulation generator 30 may deliver electrical stimulation therapy via one or more electrodes of leads 16, e.g., as stimulation pulses or continuous waveforms. Components described as processors within IMD 14, external programmer 20 or any other device described in this disclosure may each comprise one or more processors, such as one or more microprocessors, digital signal processors (DSPs), application specific integrated circuits (ASICs), field programmable gate arrays (FPGAs), programmable logic circuitry, or the like, either alone or in any suitable combination. The functions attributed to processors described herein may be embodied as software, firmware, hardware, or any combination thereof.

Stimulation generator 30 may include stimulation generation circuitry to generate stimulation pulses or waveforms and switching circuitry to switch the stimulation across different electrode combinations, e.g., in response to control by processor 26. In particular, processor 26 may control the switching circuitry on a selective basis to cause stimulation generator 30 to deliver electrical stimulation to selected electrode combinations and to shift the electrical stimulation to different electrode combinations in a first direction or a second direction when the therapy must be delivered to a different location within patient 12. In other examples, stimulation generator 30 may include multiple current sources to drive more than one electrode combination at one time. In this case, stimulation generator 30 may decrease current to the first electrode combination and simultaneously increase current to the second electrode combination to shift the stimulation therapy.

An electrode configuration, e.g., electrode combination and associated electrode polarities, may be represented by a data stored in a memory location, e.g., in memory 24, of IMD 14. Processor 26 may access the memory location to determine the electrode combination and control stimulation generator 30 to deliver electrical stimulation via the indicated electrode combination. To adjust electrode combinations, as well as amplitudes, pulse rates (frequency), or pulse widths, processor 26 may command stimulation generator 30 to make the appropriate changes to therapy according to instructions within memory 24 and rewrite the memory location to indicate the changed therapy. In other examples, rather than rewriting a single memory location, processor 26 may make use of two or more memory locations.

When activating stimulation, processor 26 may access not only the memory location specifying the electrode combination but also other memory locations specifying various stimulation parameters such as voltage or current amplitude, pulse width and pulse rate (frequency). Stimulation generator 30, e.g., under control of processor 26, then makes use of the electrode combination and parameters in formulating and delivering the electrical stimulation to patient 12.

As described above, in some examples, IMD 14 may deliver both low and high frequency stimulation in combination with each other to treat one or more patient disorders. In some examples, the frequency (or pulse rate) for the high frequency stimulation may be selected such that the stimulation substantially blocks nerve activity in a manner that prevents the nerve activity from propagating past the nerve location being stimulated. The high frequency stimulation may substantially block both afferent and efferent nerve activity from propagating past the nerve site receiving the stimulation. Example frequency or pulse rates for such high frequency stimulation may be between approximately 1 kHz and approximately 50 kHz, such as, e.g., between approximately 1 kHz and approximately 30 kHz or between approximately 3 kHz and approximately 10 kHz. In some examples, the amplitude of the high frequency stimulation may be between approximately 1 V and approximately 50 V, such as, e.g., between approximately 1 V and approximately 20 V or between approximately 3 V and approximately 10 V. The pulse width for the high frequency stimulation may be dependent, for example, on the frequency selected for the stimulation.

Again, the frequency and other stimulation parameters of the high frequency stimulation may be defined such that the high frequency stimulation is sufficient to substantially block nerve activity to prevent the nerve activity from propagating past the nerve location being stimulated. In some examples, the high frequency stimulation may be delivered as pulses in which case frequency refers of pulse rate. Other waveforms may be used, such as sinusoidal waveform or other alternating current charge-balanced waveforms to substantially block nerve activity to prevent the nerve activity from propagating past the nerve location being stimulated.

The frequency for the low frequency stimulation may be less than the frequency of the high frequency stimulation. In some examples, the frequency of the low frequency stimulation may be between approximately 1 Hz and approximately 200 Hz, such as, e.g., between approximately 1 Hz and approximately 100 Hz, or between approximately 3 Hz and approximately 50 Hz. In an example in which the low frequency stimulation is delivered to a site different from that the high frequency stimulation, the amplitude of the low frequency stimulation may between approximately 0.2 V and approximately 10 V, such as, e.g., between approximately 0.5 V and approximately 5 V or between approximately 1 V and approximately 3 V, and the pulse width of the low frequency may be between approximately 10 microseconds and approximately 2 milliseconds, such as, e.g., between approximately 50 microseconds and approximately 1 millisecond or between approximately 50 microseconds and 300 microseconds. In an example when the stimulation is delivered in envelopes including a plurality of high frequency pulses to single site, the amplitude of the envelope is that of the high frequency stimulation defining the envelope. The duration of time that the high frequency stimulation defining the envelope (the duration that the high frequency stimulation is turned "on") may be between approximately 100 microseconds and approximately 10 seconds, such as, e.g., between approximately 1 millisecond and approximately 1 second. The duration of time between envelopes (the duration that the high frequency stimulation is turned "off") may be at least approximately 500 microseconds, such as, e.g., at least approximately 1 millisecond.

Processor 26 accesses stimulation parameters in memory 24, e.g., as programs and groups of programs. Upon selection of a particular program group, processor 26 may control stimulation generator 30 to generate and deliver stimulation according to the programs in the groups, e.g., simultaneously or on a time-interleaved basis. A group may include a single program or multiple programs. As mentioned previously, each program may specify a set of stimulation parameters, such as amplitude, pulse width and pulse rate. In addition, each program may specify a particular electrode combination for delivery of stimulation. Again, the electrode combination may specify particular electrodes in a single array or multiple arrays, e.g., on a single lead or among multiple leads. Processor 26 also may control telemetry circuit 28 to send and receive information to and from external programmer 20.

Sensing module 32 may be configured to monitor one or more signals from one or more electrode on lead 16 in order to monitor electrical activity at one more locations in patient 12, e.g., via electrogram (EGM) signals. For example, sensing module 32 may be configured to monitor one or more electrical signals from electrode(s) on lead 16 at nerve sites locations. Such electrical signals may be intrinsic or evoked by delivery of stimulation by IMD 14. Signals sensed via a particular electrode may be made with reference to another electrode on a lead or an electrode on the housing of IMD 16. Sensing module 32 may also include a switch module to select which of the available electrodes, or which pairs or combinations of electrodes, are used to sense intrinsic or activity evoked, e.g., by PNS.

Signals produced by the sense amplifiers may be converted from analog signals to digital signals by analog-to-digital converters (ADCs) provided by sensing module 32. The digital signals may be stored in memory for analysis on-board the IMD 14 or remote analysis by a programmer 20 or other device. Sensing module 32 may include a digital signal processor (DSP) that implements any of a variety of digital signal processing features such as digital amplifiers, digital filters, and the like.

IMD 14 wirelessly communicates with external programmer 20, e.g., a patient programmer or a clinician programmer, or another device by radio frequency (RF) communication or proximal inductive interaction of IMD 14 with external programmer 20. Telemetry circuit 28 may send information to and receive information from external programmer 20 on a continuous basis, at periodic intervals, at non-periodic intervals, or upon request from the stimulator or programmer. To support RF communication, telemetry circuit 28 may include appropriate electronic components, such as one or more antennas, amplifiers, filters, mixers, encoders, decoders, and the like.

Power source 34 delivers operating power to the components of IMD 14. Power source 34 may include a small rechargeable or non-rechargeable battery and a power generation circuit to produce the operating power. Recharging may be accomplished through proximal inductive interaction between an external charger and an inductive charging coil within IMD 14. In some examples, power requirements may be small enough to allow IMD 14 to utilize patient motion and implement a kinetic energy-scavenging device to trickle charge a rechargeable battery. In other examples, traditional batteries may be used for a limited period of time. As a further alternative, an external inductive power supply could transcutaneously power IMD 14 when needed or desired.

Figure 3:
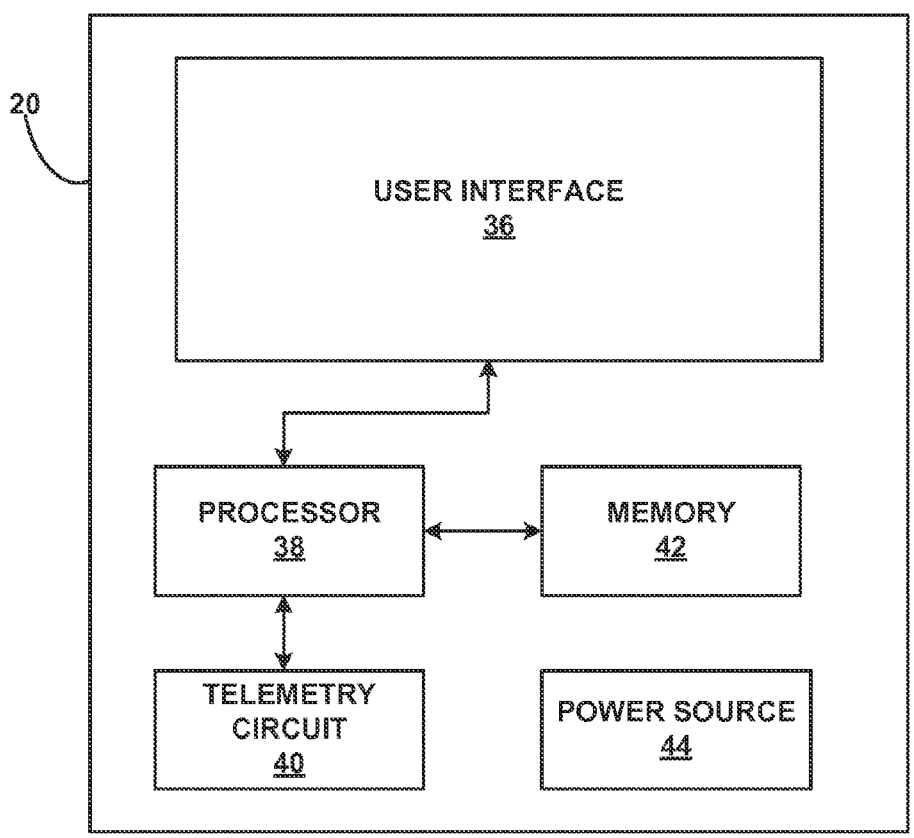
FIG. 3 is a functional block diagram illustrating various components of an example external programmer for an implantable medical device.
Figure 4:
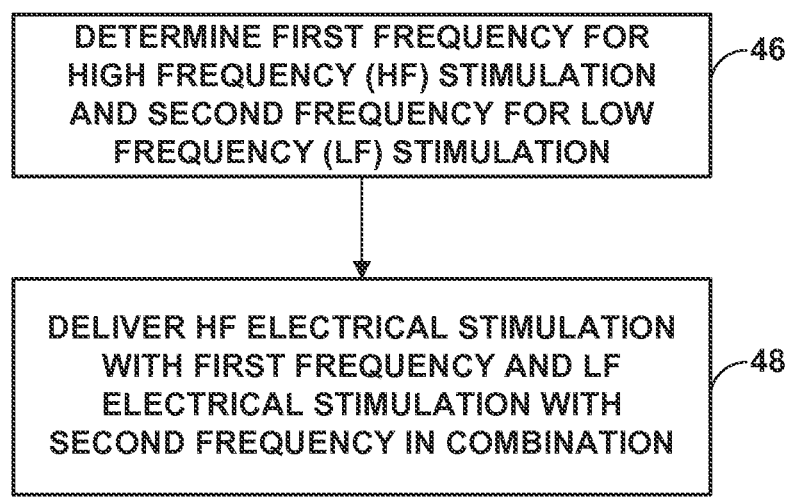
FIG. 4 is a flow diagram illustrating an example technique for delivering therapy to a patient.

FIG. 3 is a functional block diagram illustrating various components of an external programmer 20 for IMD 14. Programmer 20 may be a handheld computing device, a workstation or another dedicated or multifunction computing device. For example, programmer 20 may be a general purpose computing device (e.g., a personal computer, personal digital assistant (PDA), cell phone, and so forth) or may be a computing device dedicated to programming the IMD. As shown in FIG. 4, external programmer 20 includes user interface 36, processor 38, telemetry circuit 40, memory 42, and power source 44. External programmer 20 may be embodied as patient programmer or clinician programmer.

Processor 38 processes instructions by memory 42 and may store user input received through user interface 36 into the memory when appropriate for the current therapy. In addition, processor 38 provides and supports any of the functionality described herein with respect to each example of user interface 36. Processor 38 may comprise any one or more of a microprocessor, DSP, ASIC, FPGA, or other digital logic circuitry, and the functions attributed to programmer 38 may be embodied as software, firmware, hardware or any combination thereof.

Memory 42 may include any one or more of a RAM, ROM, EEPROM, flash memory or the like. Memory 42 may include instructions for operating user interface 36, telemetry module 40 and managing power source 44. Memory 42 may store program instructions that, when executed by processor 38, cause processor 38 and programmer 20 to provide the functionality ascribed to them herein. Memory 42 also includes instructions for generating and delivering programming commands to IMD 14. Memory 42 may also include a removable memory portion that may be used to provide memory updates or increases in memory capacities. A removable memory may also allow patient data to be easily transferred to another computing device, or to be removed before programmer 20 is used to program therapy for another patient.

Memory 42 may be considered, in some examples, a non-transitory computer-readable storage medium comprising instructions that cause one or more processors, such as, e.g., processor 38 and/or processor 26, to implement one or more of the example techniques described in this disclosure. The term "non-transitory" may indicate that the storage medium is not embodied in a carrier wave or a propagated signal. However, the term "non-transitory" should not be interpreted to mean that memory 42 is non-movable. As one example, memory 42 may be removed from IMD programmer 20, and moved to another device. In certain examples, a non-transitory storage medium may store data that can, over time, change (e.g., in RAM).

A clinician, patient 12, or another user (e.g., a patient caretaker) interacts with user interface 36 in order to manually change the stimulation parameter values of a program, change programs within a group, or otherwise communicate with IMD 14 or IMD 15. User interface 36 may include a screen and one or more mechanisms, such as buttons, as in the example of patient programmer 30, that allow external programmer 20 to receive input from a user. Alternatively, user interface 36 may additionally or only utilize a touch screen display, as in the example of clinician programmer 60. The screen may be a liquid crystal display (LCD), dot matrix display, organic light-emitting diode (OLED) display, touch screen, or any other device capable of delivering and/or accepting information.

Processor 38 controls user interface 36, retrieves data from memory 42 and stores data within memory 42. Processor 38 also controls the transmission of data through telemetry circuit 40 to IMDs 14 or 26. Memory 42 includes operation instructions for processor 38 and data related to patient 12 therapy.

Telemetry circuit 40 allows the transfer of data to and from IMD 14 or IMD 15. Telemetry circuit 40 may communicate automatically with IMD 14 at a scheduled time or when the telemetry circuit detects the proximity of the stimulator. Alternatively, telemetry circuit 40 may communicate with IMD 14 when signaled by a user through user interface 36. To support RF communication, telemetry circuit 40 may include appropriate electronic components, such as amplifiers, filters, mixers, encoders, decoders, and the like. Power source 44 may be a rechargeable battery, such as a lithium ion or nickel metal hydride battery. Other rechargeable or conventional batteries may also be used. In some cases, external programmer 20 may be used when coupled to an alternating current (AC) outlet, i.e., AC line power, either directly or via an AC/DC adapter. Although not shown in FIG. 3, in some examples, external programmer 20 may include a charger module capable of recharging a power source, such as a rechargeable battery that may be included in power source 34 of IMD 14. Hence, in some cases, the programmer may be integrated with recharging components to form a combined programmer/recharger unit.

As described above, some examples of the disclosure relate to techniques for delivering high frequency and low frequency electrical stimulation to a patient in combination with each other, e.g., to treat one or more sensory or motors disorders of patient. The combined delivery may be configured to modulate pathological nerve activity to non-pathological nerve activity. In particular, the high frequency stimulation may be configured to substantially block nerve activity at one more nerve sites of a patient. Additionally, the low and high frequency stimulation may be configured such that the nerve activity proximal (in the case of afferent nerve disorders) and/or distal (in the case of efferent nerve disorders) the nerve site where the high frequency stimulation is delivered is nerve activity that mimics non-pathological nerve activity.

FIG. 4 is a flow diagram illustrating an example technique for delivering electrical stimulation to patient 12, e.g., to treat one or more sensory or motor disorder characterized by pathological overactive nerve activity. For ease of illustration, the example technique of FIG. 4 is described with regard to system 10 of FIG. 1. However, such a technique may be employed in any suitable system configured to deliver electrical stimulation to a patient. Furthermore, while example technique of FIG. 4 is described primarily with reference to processor 26 of IMD 14, in other examples, a processor of another device, such as processor 38 of programmer 20, may perform one or more of such steps in combination with, or in lieu of, processor 26 in accordance with some examples of the disclosure.

As shown in FIG. 4, processor 26 may determine a first frequency for high frequency (HF) electrical stimulation and a second frequency, which is less than the first frequency, for low frequency (LF) stimulation (48). For example, processor 26 may determine the value by accessing information stored in memory 24 that defines the first and second frequencies. In some examples, a user such as a clinician may define the first and second frequencies values in memory 24, along with other stimulation parameters for the LF and HF stimulation, e.g., via programmer 20 during a programming session. In other examples, the first and second frequencies values may be stored in memory 42 of programmer 20, and accessed by processor 26 via telemetry circuit 28.

Upon determining the first and second frequencies (46), processor 26 may control stimulation generator 30 to deliver the LF and HF stimulation therapy to one or more nerve sites of patient 12 via lead 16(48). Lead 16 may be positioned to deliver stimulation via one or electrodes adjacent to one or more nerves sites of patient 12. The one or more nerves sites may be part of a neural pathway that exhibits pathological overactive nerve activity associated with one or more patient disorders.

As noted above, in some examples, IMD 14 may deliver stimulation to treat one or more sensory disorders characterized by abnormal overactive afferent activity. Symptoms of such sensory disorders may result from, or be associated with, overactive afferent nerve activity of a patient, e.g., in the sense that symptoms of the sensory disorder may frequently occur or manifest themselves when the afferent nerve activity of the patient is elevated. The overactive afferent nerve activity may cause pain, overwhelm central processing, and/or inhibit associated neural activities through reflex pathways. Example sensory disorders characterized by pathological overactive afferent activity may include chronic pelvic pain, interstitial cystitis, abacterial chronic prostatitis (Type IIIB), neuralgias, and other chronic pain conditions.

In addition to sensory disorders, IMD 14 may deliver stimulation to treat one or more motor disorders characterized by abnormal overactive efferent activity. Symptoms of such motor disorders may result from, or be associated with, overactive efferent nerve activity of a patient, e.g., in the sense that symptoms of the motor disorder may frequently occur or manifest themselves when the efferent nerve activity of the patient is elevated. The overactive efferent nerve activity may cause muscle spasms, uncontrollable or unintended movement, muscle cramps and pain, poor coordination for function, poor gait and balance, voiding disorders, and/or bowel movement disorders. Example motor disorders characterized by pathological overactive efferent activity may include spasticity, tics, choreas, intractable hiccups, and the like.

In each case, the HF stimulation delivered by IMD 14 to one or more nerve sites may be configured to substantially block pathological nerve activity at the one more nerve sites of a neural pathway. For example, the HF stimulation may have a frequency selected to inhibit spontaneous nerve activity of the nerve site along the neural pathway. Such HF stimulation may blocks intrinsic nerve firing at target nerve site to prevent efferent and afferent nerve activity from propagating past the one or more nerve sites receiving the HF stimulation. In some examples, the HF stimulation creates a local nerve conduction block.

In some examples, the frequency for the HF stimulation may be between 1 kHz and approximately 50 kHz, such as, e.g., between approximately 1 kHz and approximately 30 kHz or between approximately 3 kHz and approximately 10 kHz. In some examples, the amplitude of the high frequency stimulation may be between approximately 1 V and approximately 50 V, such as, e.g., between approximately 1 V and approximately 20 V or between approximately 3 V and approximately 10 V. The pulse width for the high frequency stimulation may be dependent, for example, on the frequency selected for the stimulation. Again, the frequency and other stimulation parameters of the high frequency stimulation may be defined such that the high frequency stimulation is sufficient to substantially block nerve activity to prevent the nerve activity from propagating past the nerve location being stimulated.

In addition to the HF stimulation to substantially blocking pathological overactive nerve activity, the combination of LF stimulation and HF stimulation may be configured to result in nerve activity that mimics non-pathological nerve activity. In an example where the low frequency stimulation is delivered to a nerve site separate from the nerve site of the high frequency stimulation site, the non-pathological nerve activity may be exhibited proximal (e.g., in the case of a afferent nerve disorder) or distal (e.g., in the case of a efferent nerve disorder) the one or more nerve sites receiving HF stimulation that substantially blocks pathological overactive nerve activity. In an example in which the combination of first and second therapies is defined by stimulation in the form of envelopes of high frequency pulses delivered to a nerve site, the frequency and duration of the envelopes may be selected such that non-pathological nerve activity may be exhibited at the nerve site. In such a case, non-pathological nerve activity may be exhibited proximal (e.g., in the case of a afferent nerve disorder) or distal (e.g., in the case of a efferent nerve disorder) the nerve site. In some examples, the combination of LF and HF stimulation may result in nerve activity that is at a level less than the pathological nerve activity. The non-pathological nerve activity may be a level of nerve activity that may be considered normal, at least to the extent that manifestation of symptoms of the patient disorder being treated are reduced or even eliminated entirely.

As will be described below with regard to FIGS. 5, 6A, and 6B, in some examples, processor 26 may control stimulation generator 30 deliver the HF stimulation via one or more first electrodes on lead 16 to a first nerve site. The HF stimulation may be multi-polar stimulation, e.g., using two or more electrodes on lead 16, or unipolar stimulation, e.g., using one electrode on lead 16 and a can electrode of IMD 14. At substantially the same time, deliver unipolar or multi-polar LF stimulation via one or more second electrodes on lead 16 to a second nerve site that is proximal or distal the first nerve site with regard to the neural pathway. For example, in the case of pathological afferent activity, the second nerve site may be proximal the first nerve site. As another example, in the case of pathological efferent activity, the second nerve site may be distal the first nerve site. Again, processor 26 may control the stimulation at each site to be either unipolar or multipolar. In such a configuration, the HF stimulation may substantially block the pathological nerve activity at the first nerve site and the LF stimulation may be configured to activate nerve fibers in a manner that induces nerve activity that mimics non-pathological nerve activity.

As will be described below with regard to FIGS. 7 and 8, in another example, processor 26 may control stimulation generator 30 to deliver the HF and LF electrical stimulation therapies via lead to a single nerve site of the patient, e.g., using the same electrode(s) on lead 16. In such examples, the HF and LF therapies may be defined by a stimulation signal including a plurality of envelopes (or bursts) delivered according to the low frequency defined for the LF stimulation. Within each envelope is a plurality of individual stimulation pulses delivered according to the high frequency defined for the HF stimulation. During the time period, an envelope is delivered by IMD 14, the nerve activity at the nerve site may be substantially blocked. The frequency and duration that the envelopes are delivered may be selected such that the nerve activity not blocked by the envelopes (e.g., the nerve activity that occurs during the time that an envelope is not being delivered to the site) over a period of time mimics non-pathological nerve activity.

Figure 5:
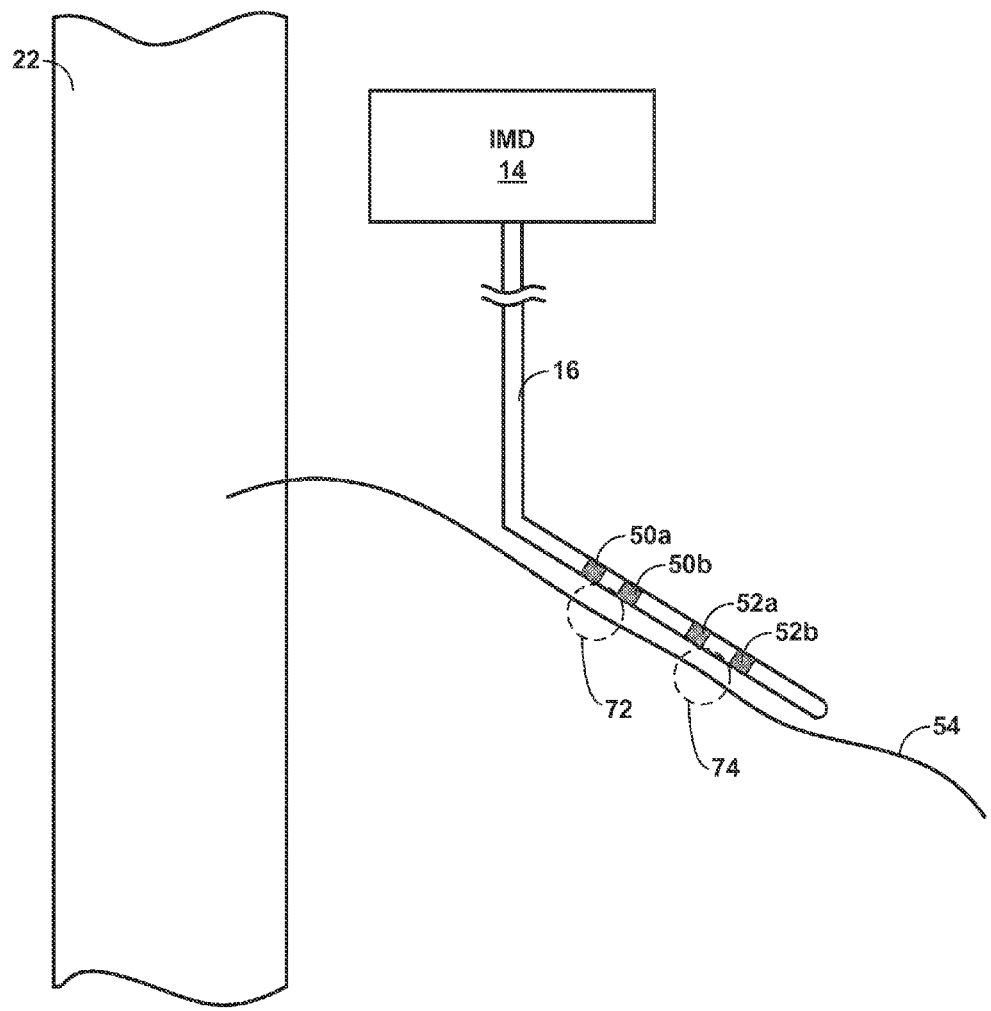
FIG. 5 is a conceptual diagram illustrating an example implantable stimulation system configured to deliver stimulation therapy to a patient.

FIG. 5 is a conceptual diagram illustrating example stimulation system including IMD 14 and lead 16, which may be substantially the same or similar to that described above. As shown, lead 16 includes electrode 50a and 50b (referred to collectively as "electrodes 50") and electrodes 52a and 52b (referred to collectively as "electrodes 52") located on a distal portion of lead 16. Lead 16 is implanted adjacent to peripheral nerve 54 in a location that allows electrodes 50 to deliver stimulation to nerve site 72 on peripheral nerve 54 and allows electrodes 52 to deliver stimulation to nerve site 72 on peripheral nerve 54. Peripheral nerve 54 is connected to spinal cord 22, and may exhibit pathological overactive nerve activity associated with a patient disorder to be managed by electrical stimulation.

Depending on the whether the pathological overactive nerve activity is efferent or afferent nerve activity, one of electrode pairs 50 and 52 may deliver bi-polar HF stimulation and the other of electrode pairs 50 and 52 may deliver bi-polar LF stimulation in combination with the HF stimulation. For example, in the case of pathological overactive afferent nerve activity (e.g., associated with a sensory disorder), processor 26 of IMD 14 may control stimulation generator 30 to delivery HF stimulation via electrodes 52 to nerve site 74 and LF stimulation via electrodes 50 to nerve site 72. The HF stimulation delivered to nerve site 74 may be configured to substantially block nerve activity at nerve site 74 to prevent nerve activity from propagating past nerve site 74. At the same time, the delivery of the LF stimulation to nerve site 72 via electrodes 50 may be configured to induce nerve activity that mimics non-pathological afferent nerve activity at nerve site 72, which may propagate proximally from nerve site 72 along the neural pathway of peripheral nerve 54 to spinal cord 22. In some examples, the LF stimulation may allow for substantially normal reflex functions disturbed by the sensory disorder being treated.

Conversely, in the case of pathological overactive efferent nerve activity (e.g., associated with a motor disorder), processor 26 of IMD 14 may control stimulation generator 30 to delivery LF stimulation via electrodes 52 to nerve site 74 and HF stimulation via electrodes 50 to nerve site 72. The HF stimulation delivered to nerve site 72 may be configured to substantially block nerve activity at nerve site 72 to prevent nerve activity from propagating past nerve site 72. In some examples, HF stimulation may block pathological motor activity of central origin. At the same time, the delivery of the LF stimulation to nerve site 74 via electrodes 52 may be configured to induce nerve activity that mimics non-pathological nerve activity at nerve site 74, which may propagate distally from nerve site 74 along the neural pathway of peripheral nerve 54 away from spinal cord 22. In some examples, the LF stimulation may be configured to restore motor function disturbed by the motor disorder being treated.

In each example, IMD 14 may deliver electrical stimulation to peripheral nerve 54 to substantially block overactive pathological nerve activity via HF stimulation and induce nerve activity that mimics non-pathological nerve activity via LF stimulation. Although the configuration of FIG. 5 illustrates stimulation of nerve sites 72 and 74 via bi-polar stimulation, nerve sites 72 and 74 may be stimulated via any suitable unipolar or multipolar electrode configuration using electrodes on one or multiple leads.

Figure 6A:
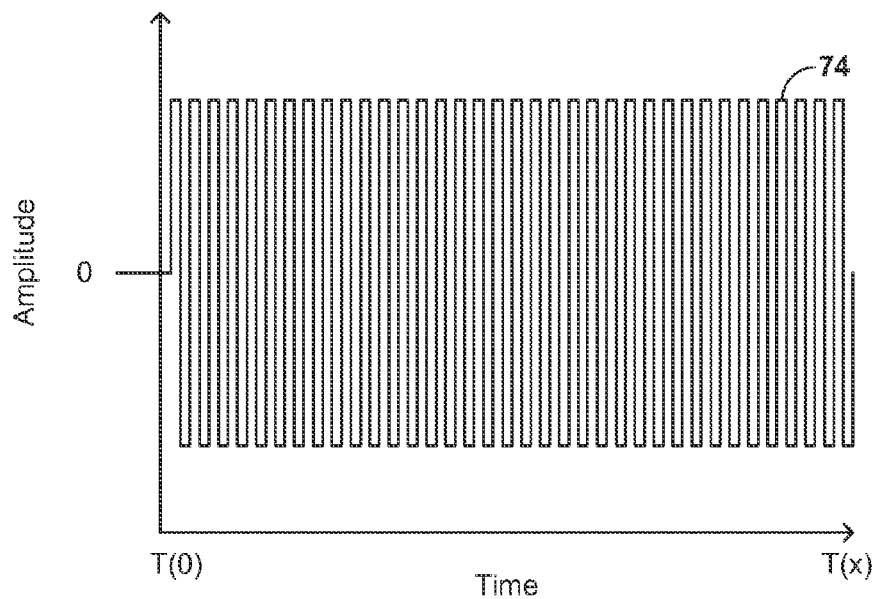
FIGS. 6A and 6B are conceptual diagrams illustrating the timing an example stimulation therapy delivered to a patient.
Figure 6B:
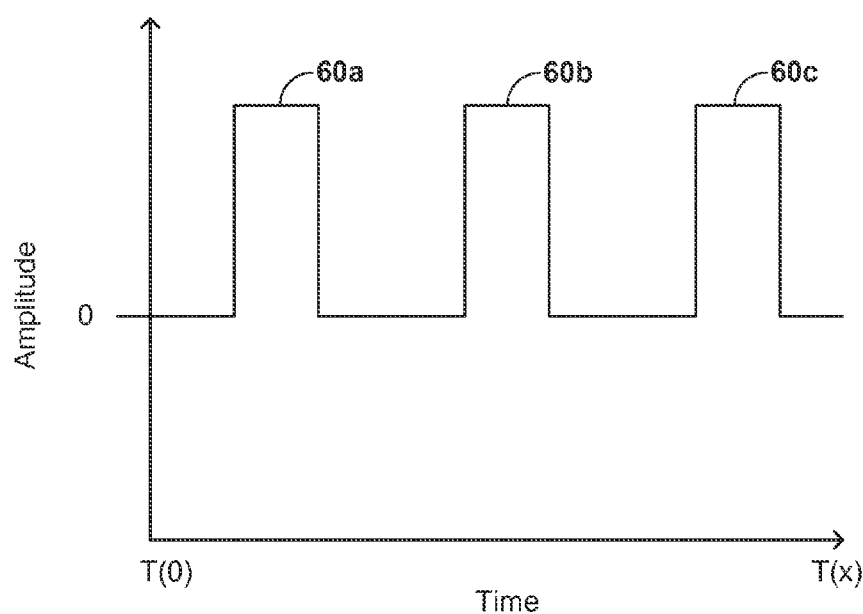

FIGS. 6A and 6B are conceptual diagrams illustrating the timing of an example stimulation therapy delivered to patient 12, e.g., as described above with regard to FIG. 5. FIG. 6A illustrates the timing of the HF stimulation and FIG. 6B illustrate the timing of the LF stimulation that may be delivered to patient 12 by IMD 14. As shown in FIG. 6B, the HF stimulation includes a plurality of pulses (a single pulse 74 is labeled in FIG. 6A). In some examples, the polarity and amplitude of the pulses may be selected such that the HF stimulation is substantially charge balanced. Although no time delay is shown between adjacent pulses, in some examples, there may be some time delay. Although the high stimulation is shown in FIG. 6A is shown as a serious of alternating charge, block pulses, the high frequency stimulation could be a sinusoidal waveform or alternating charged balanced waveform.

Again, the HF stimulation may be configured to substantially block overactive pathological nerve activity. In some examples, the frequency for the HF stimulation in FIG. 6A may be between approximately 1 kHz and approximately 50 kHz, such as, e.g., between approximately 1 kHz and approximately 30 kHz or between approximately 3 kHz and approximately 10 kHz. In some examples, the amplitude of the high frequency stimulation may be between approximately 1 V and approximately 50 V, such as, e.g., between approximately 1 V and approximately 20 V or between approximately 3 V and approximately 10 V. The pulse width for the high frequency stimulation may be dependent, for example, on the frequency selected for the stimulation.

As shown in FIG. 6B, the LF stimulation is delivered to an upstream nerve site over the same time period that the HF stimulation is delivered. The LF stimulation includes pulses 60a, 60b, and 60c (collectively "pulses 60"). Pulses 60 may be configured such that the delivery of the LF stimulation results in nerve activity that mimics non-pathological nerve activity. In some examples, the frequency of pulses 60 may be between approximately 1 Hz and approximately 200 Hz, such as, e.g., approximately 1 Hz and approximately 100 Hz, or between approximately 3 Hz and approximately 50 Hz. The amplitude of the low frequency stimulation may between approximately 0.2 V and approximately 10 V, such as, e.g., between approximately 0.5 V and approximately 5 V or between approximately 1 V and approximately 3 V, and the pulse width of the low frequency may be between approximately 10 microseconds and approximately 2 milliseconds, such as, e.g., between approximately 50 microseconds and approximately 1 millisecond or between approximately 50 microseconds and 300 microseconds. The resulting nerve activity that mimics non-pathological nerve activity distal (e.g., in the case of efferent activity) or proximal (e.g., in the case of afferent activity) the HF stimulation nerve site. The frequency, inter-pulse interval, pulse width, and/or amplitude of the LF stimulation may be fixed or variable. For example, as the non-pathological nerve activity may not be fixed but may instead vary, the pulse width, frequency, inter-pulse interval, and/or amplitude of the LF stimulation may be varied in such a fashion in order to mimic such non-pathological nerve activity. The HF and LF stimulation of FIGS. 6A and 6B may be delivered substantially continuously or periodically to patient 12. In some examples, HF and LF stimulation may be delivered to patient 12 according to a pre-program schedule and/or on an on demand basis (e.g., based on monitor patient parameters or direction of patient 12 via programmer 20).

Figure 7:
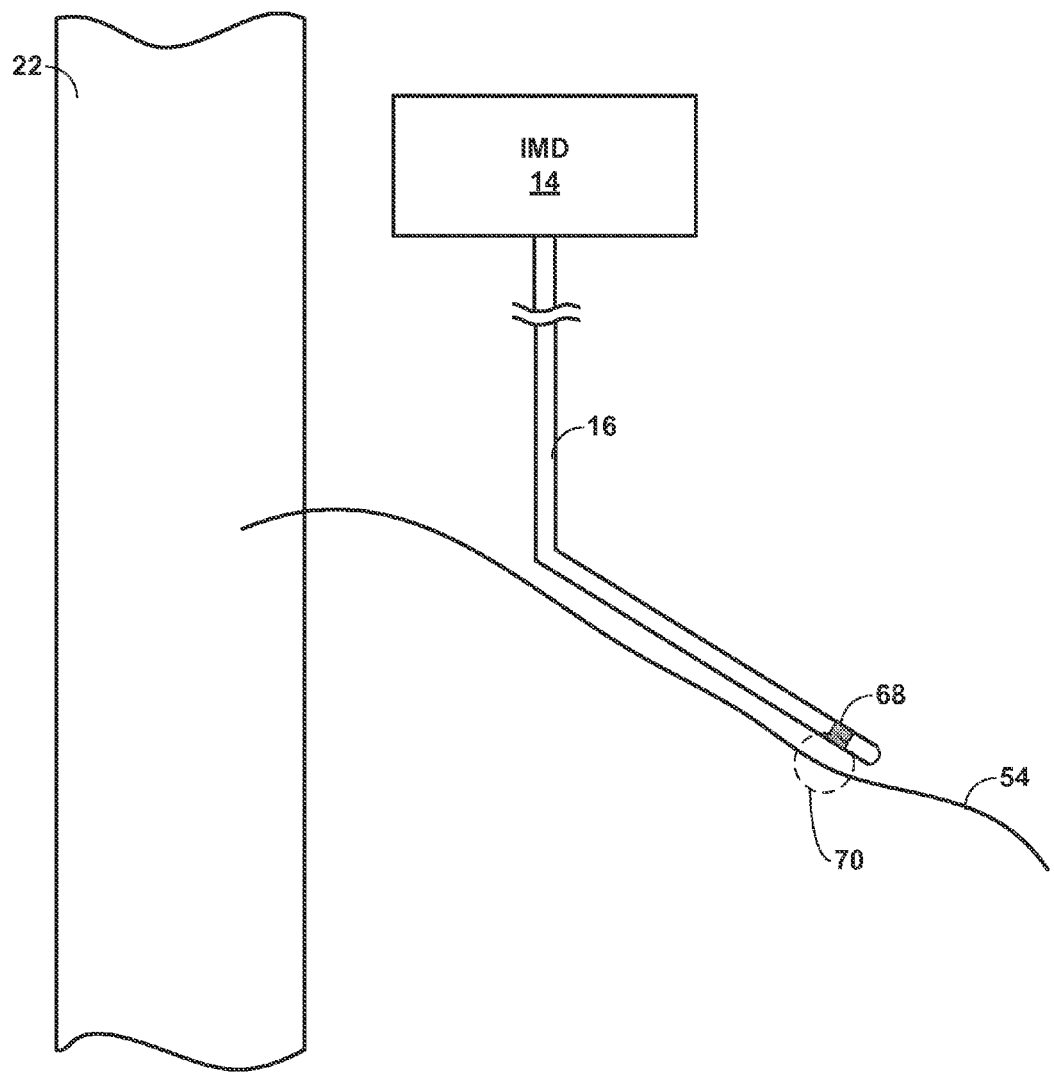
FIG. 7 is a conceptual diagram illustrating another example implantable stimulation system configured to deliver stimulation therapy to a patient.

FIG. 7 is a conceptual diagram illustrating another example implantable stimulation system including IMD 14 and lead 16. IMD 14 and lead 16 may be substantially similar to that described with regard to FIG. 5. However, lead 16 includes a single electrode 68 which is located proximate to peripheral nerve 54 to deliver unipolar stimulation to nerve site 70. Again, peripheral nerve 54 is connected to spinal cord 22, and may exhibit pathological overactive nerve activity associated with a patient disorder to be managed by electrical stimulation.

In the configuration of FIG. 7, processor 26 may control stimulation generator 30 to deliver the HF and LF electrical stimulation therapies via electrode 68 to nerve site 70. In such examples, the HF and LF therapies may be defined by a stimulation signal including a plurality of envelopes (or bursts) delivered according to the low frequency defined for the LF stimulation. Within each envelope is a plurality of individual stimulation pulses delivered according to the high frequency defined for the HF stimulation. During the time period an envelope is delivered by IMD 14, the nerve activity at nerve site 70 may be substantially blocked. The frequency and length that the envelopes are delivered may be selected such that the nerve activity not blocked by the envelopes (e.g., the nerve activity that occurs during the time that an envelope is not being delivered to the site) over a period of time mimics non-pathological nerve activity.

Although the configuration of FIG. 7 illustrates stimulation of nerve sites 70 via unipolar stimulation, nerve site 70 may be stimulated via any suitable unipolar or multipolar electrode configuration using electrodes on one or multiple leads.

Figure 8:
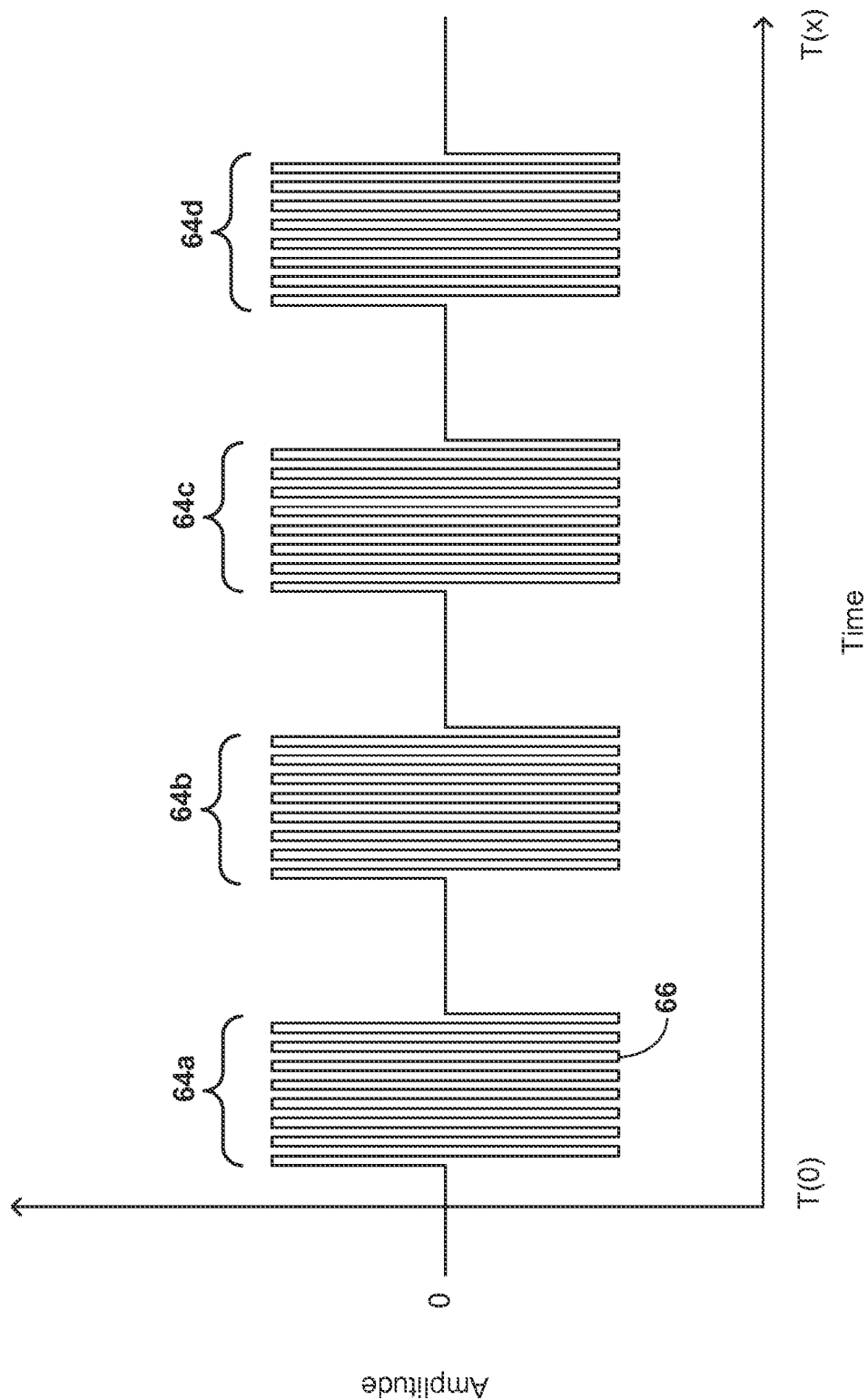
FIG. 8 is a conceptual diagram illustrating the timing of another example stimulation therapy delivered to a patient.

FIG. 8 is a conceptual diagram illustrating the timing of another example stimulation therapy delivered to a patient, e.g., as described with regard to FIG. 7. Processor 26 may control stimulation generator 30 to deliver electrical stimulation to nerve site 70 according to the waveform shown in FIG. 8. As shown, the electrical stimulation includes envelopes 64a, 64b, 64c, and 64d (collectively "envelopes 64"). Each envelope includes a plurality of pulses (a single pulse 66 is labeled in envelope 64a). In some examples, the polarity and amplitude of the pulses of each envelope 64 may be selected such that each envelope 64 is substantially charge balanced. Although no time delay is shown between adjacent pulses in envelopes 64, in some examples, there may be some time delay. Although the high stimulation is shown in FIG. 6A is shown as a serious of alternating charge, block pulses, the high frequency stimulation could be a sinusoidal waveform or alternating charged balanced waveform.

Again, the HF stimulation delivered during each envelope 64 may be configured to substantially block overactive pathological nerve activity. In some examples, the frequency of the stimulation pulses in envelopes 64 may be between approximately 1 kHz and approximately 50 kHz, such as, e.g., between approximately 1 kHz and approximately 30 kHz or between approximately 3 kHz and approximately 10 kHz. In some examples, the amplitude of the high frequency stimulation may be between approximately 1 V and approximately 50 V, such as, e.g., between approximately 1 V and approximately 20 V or between approximately 3 V and approximately 10 V. The pulse width for the high frequency stimulation may be dependent, for example, on the frequency selected for the stimulation. Again, the frequency and other stimulation parameters of the high frequency stimulation may be defined such that the high frequency stimulation is sufficient to substantially block nerve activity to prevent the nerve activity from propagating past the nerve location being stimulated.

Processor 26 may control stimulation generator 30 to deliver envelopes 64 at frequency such that the nerve activity not blocked during the delivery of envelopes 64 (e.g., the nerve activity that occurs during the time that envelopes 64 are not being delivered to target site 70) over a period of time mimics non-pathological nerve activity. In some examples, the frequency of envelopes 64 may be 1 Hz and approximately 200 Hz, such as, e.g., between approximately 1 Hz and approximately 100 Hz, or between approximately 3 Hz and approximately 50 Hz. The amplitude of the envelopes 64 is that of the high frequency stimulation defining envelope 64. The duration of time that the high frequency stimulation defining envelopes 64 (the duration that the high frequency stimulation is turned "on") may be between approximately 100 microseconds and approximately 10 seconds, such as, e.g., between approximately 1 millisecond and approximately 1 second. The duration of time between envelopes 64 (the duration that the high frequency stimulation is turned "off") may be at least approximately 500 microseconds, such as, e.g., at least approximately 1 millisecond.

In the case of overactive pathological afferent activity, the envelop signal frequency may titrated to break down the pain sensation associated with the patient disorder. In some examples, envelopes 64 can also have variable intervals between the respective envelopes 64 such that the remaining spontaneous nerve activity not blocked by envelopes 64 resembles or mimics physiological afferent activity. Conversely, in the case of pathological efferent nerve activity (e.g., in the case of some motor disorders), envelopes 64 may be delivered to block nerve conduction to break down the tetanic motor movements associated with the pathological efferent nerve activity.

While examples of the disclosure are described with regard to delivering stimulation therapy to one or more locations to treat sensory or motor disorders characterized by overactive nerve activity, the treatment of other types of disorders are contemplated. For example, examples of the described stimulation may be delivered as therapies to treat one or more other patient conditions, such as, e.g., voiding disorders, bowel movement disorders, spastic colon, irritable bowel syndrome (IBS), interstitial cystitis, autonomic disorders, (such as, hypertension, hyperhidrosis), epilepsy, Parkinson's disease, Alzheimer's disease, dystonia, schizophrenia, obsessive compulsive disorder, and depression.

Furthermore, in some examples, the described HF and LF stimulation may be delivered to more than one nerve site. For example, in the case of LF stimulation being delivered at a location different from that of the HF stimulation, the HF stimulation and/or LF stimulation may be delivered to multiple nerve site along connected neural pathways. In some examples, HF stimulation may be delivered to multiple branches of a nerve in combination to the delivery of LF stimulation to the trunk of the nerve, or vice versa. For example, for pudendal nerve stimulation, LF stimulation may be delivered to the pudendal nerve trunk and HF stimulation may be delivered to nerve sites on two or more pudendal branches, e.g., dorsal genital nerve, perineal nerve, inferior rectal nerve. The HF stimulation could be delivered to each branch at the same time or individually, e.g., based on pain being experienced by a patient.

The techniques described in this disclosure may be implemented, at least in part, in hardware, software, firmware or any combination thereof. For example, various aspects of the techniques may be implemented within one or more microprocessors, DSPs, ASICs, FPGAs, or any other equivalent integrated or discrete logic circuitry, as well as any combinations of such components, embodied in programmers, such as physician or patient programmers, stimulators, or other devices. The term "processor" or "processing circuitry" may generally refer to any of the foregoing logic circuitry, alone or in combination with other logic circuitry, or any other equivalent circuitry.

When implemented in software, the functionality ascribed to the systems and devices described in this disclosure may be embodied as instructions on a computer-readable medium such as RAM, ROM, NVRAM, EEPROM, FLASH memory, magnetic media, optical media, or the like. The instructions may be executed to support one or more aspects of the functionality described in this disclosure.

If implemented in software, the techniques described in this disclosure may be stored on or transmitted over as one or more instructions or code on a computer-readable medium. Computer-readable media may include non-transitory computer storage media or communication media including any medium that facilitates transfer of a computer program from one place to another. Data storage media may be any available media that can be accessed by one or more computers or one or more processors to retrieve instructions, code and/or data structures for implementation of the techniques described in this disclosure. By way of example, and not limitation, such data storage media can comprise RAM, ROM, EEPROM, CD-ROM or other optical disk storage, magnetic disk storage, or other magnetic storage devices, flash memory, or any other medium that can be used to store desired program code in the form of instructions or data structures and that can be accessed by a computer. Also, any connection is properly termed a computer-readable medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. Disk and disc, as used herein, includes compact disc (CD), laser disc, optical disc, digital versatile disc (DVD), floppy disk and blu-ray disc where disks usually reproduce data magnetically, while discs reproduce data optically with lasers. Combinations of the above should also be included within the scope of computer-readable media.

The code may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor," as used herein may refer to any of the foregoing structure or any other structure suitable for implementation of the techniques described herein. Also, the techniques could be fully implemented in one or more circuits or logic elements.

In addition, it should be noted that the systems described herein may not be limited to treatment of a human patient. In alternative examples, these systems may be implemented in non-human patients, e.g., primates, canines, equines, pigs, birds, and felines. These animals may undergo clinical or research therapies that my benefit from the subject matter of this disclosure.

Many examples of the disclosure have been described. Various modifications may be made without departing from the scope of the claims. These and other examples are within the scope of the following claims.

The invention claimed is:

1. A method comprising
controlling delivery of electrical stimulation therapy to a patient via a medical device, wherein the stimulation therapy includes a plurality of pulse envelopes, each pulse envelope of the plurality of pulse envelopes including a plurality of individual pulses delivered at a first frequency, wherein the plurality of pulse envelopes are delivered at a second frequency less than the first frequency,
wherein the first frequency is configured such that the stimulation therapy substantially blocks overactive pathological nerve activity of the patient, and wherein the second frequency is configured such that nerve activity not blocked by the stimulation therapy mimics non-pathological nerve activity.

2. The method of claim 1, wherein the second frequency is between approximately 1 hertz and approximately 200 hertz.

3. The method of claim 1, wherein the first frequency is between approximately 1 kilohertz and approximately 50 kilohertz.

4. The method of claim 1, wherein the first frequency is between approximately 1 kilohertz and approximately 50 kilohertz, and the second frequency is between approximately 1 hertz and approximately 200 hertz.

5. The method of claim 1, wherein each pulse envelope of the plurality of pulse envelopes is substantially charge balanced.

6. The method of claim 1, wherein there is a time delay between adjacent pulses of the plurality of individual pulses in each pulse envelope of the plurality of pulse envelopes.

7. The method of claim 1, wherein controlling the delivery of therapy to the patient comprises controlling the delivery of therapy to the patient to treat overactive pathological afferent nerve activity, and wherein the second frequency is configured such that nerve activity not blocked by the stimulation therapy mimics non-pathological afferent nerve activity.

8. The method of claim 1, wherein controlling the delivery of therapy to the patient comprises controlling the delivery of therapy to the patient to treat overactive pathological efferent nerve activity, and wherein the second frequency is configured such that nerve activity not blocked by the stimulation therapy mimics non-pathological efferent nerve activity.

9. The method of claim 1, wherein a time delay between adjacent pulse envelopes of the plurality of pulse envelopes is greater than approximately 500 microseconds.

10. The method of claim 1, wherein the first frequency is between approximately 3 kilohertz and approximately 10 kilohertz, and the second frequency is between approximately 3 hertz and approximately 50 hertz.

11. A system comprising:
a therapy module configured to deliver electrical stimulation therapy to a patient; and
a processor configured to control the therapy module to deliver the stimulation therapy to the patient such that the stimulation therapy includes a plurality of pulse envelopes, each pulse envelope of the plurality of pulse envelopes including a plurality of individual pulses delivered at a first frequency, wherein the plurality of pulse envelopes are delivered at a second frequency less than the first frequency, wherein the first frequency is configured such that the stimulation therapy substantially blocks overactive pathological nerve activity of the patient, and wherein the second frequency is configured such that nerve activity not blocked by the stimulation therapy mimics non-pathological nerve activity.

12. The system of claim 11, wherein the second frequency is between approximately 1 hertz and approximately 200 hertz.

13. The system of claim 11, wherein the first frequency is between approximately 1 kilohertz and approximately 50 kilohertz.

14. The system of claim 11, wherein the first frequency is between approximately 1 kilohertz and approximately 50 kilohertz, and the second frequency is between approximately 1 hertz and approximately 200 hertz.

15. The system of claim 11, wherein each pulse envelope of the plurality of pulse envelopes is substantially charge balanced.

16. The system of claim 11, wherein there is a time delay between adjacent pulses of the plurality of individual pulses in each pulse envelope of the plurality of pulse envelopes.

17. The system of claim 11, wherein the processor is configured to control delivery of therapy to the patient to treat overactive pathological afferent nerve activity, and wherein the second frequency is configured such that nerve activity not blocked by the stimulation therapy mimics non-pathological afferent nerve activity.

18. The system of claim 11, wherein the processor is configured to control the delivery of therapy to the patient to treat overactive pathological efferent nerve activity, and wherein the second frequency is configured such that nerve activity not blocked by the stimulation therapy mimics non-pathological efferent nerve activity.

19. The system of claim 11, wherein a time delay between adjacent pulse envelopes of the plurality of pulse envelopes is greater than approximately 500 microseconds.

20. The system of claim 11, wherein the first frequency is between approximately 3 kilohertz and approximately 10 kilohertz, and the second frequency is between approximately 3 hertz and approximately 50 hertz.

21. A system comprising:
means for delivering electrical stimulation therapy to a patient via a medical device; and
means for controlling the delivery of electrical stimulation therapy to the patient via the medical device, wherein the stimulation therapy includes a plurality of pulse envelopes, each pulse envelope of the plurality of pulse envelopes including a plurality of individual pulses delivered at a first frequency, wherein the plurality of pulse envelopes are delivered at a second frequency less than the first frequency,
wherein the first frequency is configured such that the stimulation therapy substantially blocks overactive pathological nerve activity of the patient, and wherein the second frequency is configured such that nerve activity not blocked by the stimulation therapy mimics non-pathological nerve activity.

22. A non-transitory computer-readable storage medium comprising instructions that cause a processor to:
control a therapy module to deliver electrical stimulation therapy to a patient via a medical device, wherein the stimulation therapy includes a plurality of pulse envelopes, each pulse envelope of the plurality of pulse envelopes including a plurality of individual pulses delivered at a first frequency, wherein the plurality of pulse envelopes are delivered at a second frequency less than the first frequency,
wherein the first frequency is configured such that the stimulation therapy substantially blocks overactive pathological nerve activity of the patient, and wherein the second frequency is configured such that nerve activity not blocked by the stimulation therapy mimics non-pathological nerve activity.

* * * * *